United States Patent
Oda et al.

(10) Patent No.: US 11,402,328 B2
(45) Date of Patent: Aug. 2, 2022

(54) AMYLOID β OLIGOMER DETECTION METHOD, AMYLOID β OLIGOMER DETECTION DEVICE, AND AMYLOID β OLIGOMER DETECTION PROGRAM

(71) Applicant: HAMAMATSU PHOTONICS K.K., Hamamatsu (JP)

(72) Inventors: Akinori Oda, Hamamatsu (JP); Hiroshi Satozono, Hamamatsu (JP); Tomomi Shinke, Hamamatsu (JP); Yohei Takata, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 685 days.

(21) Appl. No.: 15/763,935

(22) PCT Filed: Sep. 8, 2016

(86) PCT No.: PCT/JP2016/076469
§ 371 (c)(1),
(2) Date: Mar. 28, 2018

(87) PCT Pub. No.: WO2017/056905
PCT Pub. Date: Apr. 6, 2017

(65) Prior Publication Data
US 2019/0056324 A1 Feb. 21, 2019

(30) Foreign Application Priority Data
Sep. 29, 2015 (JP) .............. JP2015-191307

(51) Int. Cl.
*G01N 21/00* (2006.01)
*G01N 21/64* (2006.01)
*G01N 33/68* (2006.01)

(52) U.S. Cl.
CPC ..... *G01N 21/6408* (2013.01); *G01N 21/6428* (2013.01); *G01N 33/6896* (2013.01);
(Continued)

(58) Field of Classification Search
CPC .................................................. G01N 21/6408
(Continued)

(56) References Cited

FOREIGN PATENT DOCUMENTS

JP  2009-544954 A  12/2009
JP  2010-120942 A  6/2010
(Continued)

OTHER PUBLICATIONS

Lindberg et al. "Steady-state and time-resolved Thioflavin-T fluorescence can report on morphological differences in amyloid fibrils formed by Ab(1-40) and Ab(1-42)" Biochemical and Biophysical Research Communications 458 (2015) 418-423 (Year: 2015).*

(Continued)

*Primary Examiner* — Christine T Mui
*Assistant Examiner* — Emily R. Berkeley
(74) *Attorney, Agent, or Firm* — Faegre Drinker Biddle & Reath LLP (57) ABSTRACT

The present invention relates to a method for detecting an amyloid β oligomer which includes a test sample and thioflavin T are brought into contact with each other, fluorescence of the thioflavin T is measured to obtain time-resolved fluorescence spectra, the time-resolved fluorescence spectrum of time period t1 to t2 and the time-resolved fluorescence spectrum of time period t3 to t4 are respectively normalized to obtain normalized spectra (t1<t2≤t3<t4), and determination is made to confirm the presence or absence of an amyloid β oligomer in the test sample on the basis of the two normalized spectra, and shifting of the normalized spectrum of time period t3 to t4 towards the low wavelength side in comparison to the
(Continued)

normalized spectrum of time period t1 to t2 indicates the presence of an amyloid β oligomer in the test sample.

4 Claims, 7 Drawing Sheets

(52) U.S. Cl.
CPC .............. *G01N 2021/6413* (2013.01); *G01N 2021/6439* (2013.01); *G01N 2333/4709* (2013.01); *G01N 2800/2821* (2013.01)

(58) Field of Classification Search
USPC ........................................................ 436/86
See application file for complete search history.

(56) References Cited

FOREIGN PATENT DOCUMENTS

| | | |
|---|---|---|
| JP | 2010-168385 A | 8/2010 |
| JP | 2012-524023 A | 10/2012 |
| JP | 2014-122846 A | 7/2014 |
| JP | 2015-166749 A | 9/2015 |
| WO | WO-2008/012101 A1 | 1/2008 |
| WO | WO-2010/119704 A1 | 10/2010 |
| WO | WO-2015/060333 A1 | 4/2015 |

OTHER PUBLICATIONS

W. Blaine Stine, Jr. et al., "Protein Structure and Folding: In Vitro Characterization of Conditions for Amyloid-β Peptide Oligomerization and Fibrillogenesis," The Journal of Biological Chemistry, 2003, pp. 11612-11622, vol. 278, No. 13.

International Preliminary Report on Patentability dated Apr. 12, 2018 for PCT/JP2016/076469.

* cited by examiner

AMYLOID β OLIGOMER DETECTION METHOD, AMYLOID β OLIGOMER DETECTION DEVICE, AND AMYLOID β OLIGOMER DETECTION PROGRAM

TECHNICAL FIELD

The present invention relates to a method for detecting an amyloid β oligomer, a device for detecting an amyloid β oligomer, and a program for detecting an amyloid β oligomer.

BACKGROUND ART

For the study of Alzheimer type dementia (hereinbelow, also referred to as "AD") which becomes a social problem, the amyloid β peptide (hereinbelow, also referred to as "Aβ") receives attention as a target for diagnosis and treatment from the viewpoint of radical treatment. That is because the intracerebral accumulation of Aβ is a condition which occurs first in AD. Aβ exhibits harmful influences on neuronal cells as it is accumulated and aggregated. Thus, for the study of the diagnosis and treatment, it is important to determine the information relating to concentration or aggregation level of Aβ.

From the recent study, it becomes evident that the toxicity of Aβ for neuronal cells is derived not from Aβ fibril in which Aβ are aggregated but rather from an aggregation precursor referred to as an Aβ oligomer (see, Patent Literature 1, for example).

As a method for detecting an Aβ oligomer, a method based on gel electrophoresis and gel filtration chromatography is disclosed in Patent Literature 2, for example. Furthermore, in Patent Literature 3 and Patent Literature 4, a method of detecting an Aβ oligomer by using an antibody is disclosed.

CITATION LIST

Patent Literature

Patent Literature 1: Japanese Unexamined Patent Publication No. 2009-544954
Patent Literature 2: Japanese Unexamined Patent Publication No. 2010-168385
Patent Literature 3: Japanese Unexamined Patent Publication No. 2009-544954
Patent Literature 4: Japanese Unexamined Patent Publication No. 2012-524023

SUMMARY OF INVENTION

Problems to be Solved by the Invention

The method for detecting an Aβ oligomer of a related art remains insufficient as it takes efforts and time for measurement or high-price reagents are required, or the like.

For example, according to the method based on gel electrophoresis and gel filtration chromatography as disclosed in Patent Literature 2, although identification of an Aβ oligomer can be easily made, there is a problem that as it takes efforts and time for measurement and the distribution of Aβ oligomer cannot be turned into an image.

Furthermore, according to the method of using an antibody as disclosed in Patent Literature 3 and Patent Literature 4, detection of an Aβ oligomer can be achieved at high sensitivity as an antibody reaction is utilized, but an antibody involving cumbersome and special experimental operations is required. Furthermore, from the viewpoint that time is also required for the measurement, it cannot be recognized as a simple and inexpensive measurement method.

In view of the problems described above, an object of the present invention is to provide a method for detecting an amyloid β oligomer by which an Aβ oligomer can be detected with convenience and low cost. Other object of the present invention is to provide also a device for detecting an amyloid β oligomer and a program for detecting an amyloid β oligomer.

Means for Solving the Problems

The present invention relates to a method for detecting an amyloid β oligomer which includes a step in which a test sample and thioflavin T are brought into contact with each other, a step in which fluorescence of the thioflavin T is measured to obtain time-resolved fluorescence spectra, a step in which the time-resolved fluorescence spectrum of time period t1 to t2 and the time-resolved fluorescence spectrum of time period t3 to t4 are respectively normalized to obtain normalized spectra, and a step in which determination is made to confirm the presence or absence of an amyloid β oligomer in the test sample on the basis of the two normalized spectra, in which t1<t2≤t3<t4, and shifting of the normalized spectrum of time period t3 to t4 towards the low wavelength side in comparison to the normalized spectrum of time period t1 to t2 indicates the presence of an amyloid β oligomer in the test sample.

The present invention is based on a novel finding that, when an Aβ oligomer is subjected to fluorescence staining with thioflavin T (hereinbelow, also referred to as "ThT"), the time-resolved fluorescence spectrum derived from the ThT shifts towards the low wavelength side over time. This shifting towards the low wavelength side is specific to an Aβ oligomer, and it is not observed from Aβ fibril. Because the detection method of the present invention is based on the above novel finding, an Aβ oligomer can be detected with convenience and low cost.

According to the above detection method, it is also possible that, in the step for determination, fluorescence ratio s1 is calculated from the value of fluorescence intensity at wavelength $\lambda 1$ of the two normalized spectra (with the proviso that, $\lambda 1 > 480$ nm) based on the following equation:

Fluorescence ratio $s1$=(Fluorescence intensity of normalized spectrum of time period $t3$ to $t4$ at wavelength $\lambda 1$)/(Fluorescence intensity of normalized spectrum of time period $t1$ to $t2$ at wavelength $\lambda 1$), and when the fluorescence ratio s1 is less than 1, it is determined that an amyloid β oligomer is present, or, when the fluorescence ratio s1 is 1 or more, it is determined that an amyloid β oligomer is absent. By having the fluorescence ratio s1 as an indicator, more objective determination can be achieved.

The above detection method also can be a method in which, in the step for determination, fluorescence ratio s2 is calculated from the value of fluorescence intensity at wavelength $\lambda 2$ of the two normalized spectra (with the proviso that, $\lambda 2 < 480$ nm) based on the following equation:

Fluorescence ratio $s2$=(Fluorescence intensity of normalized spectrum of time period $t3$ to $t4$ at wavelength $\lambda 2$)/(Fluorescence intensity of normalized spectrum of time period $t1$ to $t2$ at wavelength $\lambda 2$), and when the fluorescence ratio s2 is more than 1, it is determined that an amyloid β oligomer is present, or, when the fluorescence ratio s2 is 1 or less, it is determined that an amyloid β oligomer is absent. By having the fluorescence ratio s2 as an indicator, more objective determination can be achieved.

The above detection method also can be a method in which, in the step for determination, comparison of a peak top wavelength of the two normalized spectra is made and, when the peak top wavelength of the normalized spectrum of time period t3 to t4 is shorter than the peak top wavelength of the normalized spectrum of time period t1 to t2, it is determined that an amyloid β oligomer is present, or, when the peak top wavelength of the normalized spectrum of time period t3 to t4 is the same or longer than the peak top wavelength of the normalized spectrum of time period t1 to t2, it is determined that an amyloid β oligomer is absent. By having the peak top wavelength as an indicator, more objective determination can be achieved.

The present invention can be also recognized as a data collection method for detecting an amyloid β oligomer which includes a step in which a test sample and thioflavin T are brought into contact with each other, a step in which fluorescence of the thioflavin T is measured to obtain time-resolved fluorescence spectra, and a step in which the time-resolved fluorescence spectrum of time period t1 to t2 and the time-resolved fluorescence spectrum of time period t3 to t4 are respectively normalized to obtain normalized spectra, in which t1<t2≤t3<t4, and shifting of the normalized spectrum of time period t3 to t4 towards the low wavelength side in comparison to the normalized spectrum of time period t1 to t2 indicates the presence of an amyloid β oligomer in the test sample.

The present invention further relates to a device for detecting an amyloid β oligomer which is provided with an acquisition means for acquiring time-resolved fluorescence spectrum data of thioflavin T brought into contact with a test sample, a calculation means for calculating normalized spectra by normalizing respectively the time-resolved fluorescence spectrum of time period t1 to t2 and the time-resolved fluorescence spectrum of time period t3 to t4 from the acquired time-resolved fluorescence spectrum data, a comparison means for comparing the two normalized spectra, and a determination means for determining the presence or absence of an amyloid β oligomer in the test sample based on a comparison result, in which t1<t2≤t3<t4.

The present invention further relates to a program for detecting an amyloid β oligomer arranged to make a computer function as an acquisition means for acquiring time-resolved fluorescence spectrum data of thioflavin T brought into contact with a test sample, a calculation means for calculating normalized spectra by normalizing respectively the time-resolved fluorescence spectrum of time period t1 to t2 and the time-resolved fluorescence spectrum of time period t3 to t4 from the acquired time-resolved fluorescence spectrum data (with the proviso that, t1<t2≤t3<t4), a comparison means for comparing the two normalized spectra, and a determination means for determining the presence or absence of an amyloid β oligomer in the test sample based on a comparison result.

The present invention still further relates to a computer-readable storage medium storing the aforementioned program for detecting an amyloid β oligomer.

Effects of the Invention

According to the present invention, detection of an Aβ oligomer can be achieved with convenience and low cost. Namely, according to the present invention, identification and detection of an β oligomer which is cumbersome and requires high-price reagents in related art can be achieved by a measurement based on convenient and inexpensive fluorescence staining.

BRIEF DESCRIPTION OF DRAWINGS

FIG. 4(A) is a normalized spectrum of Aβ42 fibril. FIG. 4 (B) is a normalized spectrum of Aβ42 oligomer.

EMBODIMENTS FOR CARRYING OUT THE INVENTION

Hereinbelow, embodiments for carrying out the present invention are described in detail. However, the present invention is not limited to the embodiments that are given below.

Method for Detecting Amyloid β Oligomer

The method for detecting an amyloid β oligomer according to this embodiment includes a step in which a test sample and thioflavin T are brought into contact with each other (also referred to as a "contact step"), a step in which fluorescence of the thioflavin T is measured to obtain time-resolved fluorescence spectra (also referred to as an "acquisition step"), a step in which the time-resolved fluorescence spectrum of time period t1 to t2 and the time-resolved fluorescence spectrum of time period t3 to t4 are respectively normalized to obtain normalized spectra (also referred to as a "normalization step"), and a step in which determination is made to confirm the presence or absence of an Aβ oligomer in the test sample on the basis of the two normalized spectra (also referred to as a "determination step").

Contact Step

In the contact step, a test sample and thioflavin T are brought into contact with each other. Method for having the contact is not particularly limited, and a method used for fluorescence staining of amyloid with ThT can be used, for example.

The test sample is not particularly limited as long as it is a sample for which determination of the presence or absence of an Aβ oligomer is desired. Specific examples of the test sample include brain slice, cerebrospinal fluid, blood, and mucous membrane.

Thioflavin T is represented by the following chemical formula, and it is a known chemical compound also referred to as 4-(3,6-dimethyl-1,3-benzothiazol-3-ium-2-yl)-N,N-dimethylaniline chloride. ThT is a fluorescent pigment which is universally used for staining of amyloid (ThT staining).

[Chem. 1]

For the detection method according to this embodiment, a commercially available ThT reagent can be used without any particular limitation, for example.

ThT exhibits fluorescence having a peak wavelength near 480 nm (excitation wavelength is 405 nm, for example). Meanwhile, upon illumination of light, ThT generates a photoreaction product (fluorescent impurities) which exhibits fluorescence having a peak wavelength near 440 nm (excitation wavelength is 350 nm, for example). A commercially available ThT reagent contains the fluorescent impurities.

From the viewpoint of further enhancing the detection sensitivity of an Aβ oligomer, for the detection method according to this embodiment, it is preferable to use ThT from which the fluorescent impurities are removed. By dissolving a mixture of fluorescent impurities and ThT in a polar solvent like water under light shielding condition or red light condition and repeating liquid-liquid extraction with a non-polar solvent like hexane, for example, ThT from which the fluorescent impurities are removed can be obtained in the form in which ThT is dissolved in a polar solvent layer.

The Aβ oligomer is a precursor of Aβ fibril which is also referred to as protofibril. The Aβ oligomer is an aggregate in which an Aβ peptide monomers are aggregated, and it generally has molecular weight of 9 to 200 kDa or so. Number of the AP peptide monomer contained in an Aβ oligomer is generally 2 to 40 or so.

Acquisition Step

According to the acquisition step, fluorescence of thioflavin T which has been brought into contact with a test sample is measured to obtain time-resolved fluorescence spectra.

The time-resolved fluorescence spectrum of thioflavin T which has been brought into contact with a test sample can be obtained by a known method. Specifically, it can be obtained by, using a fluorescence lifetime measurement device, illuminating ThT which has been brought into contact with a test sample with light having a wavelength of 400 to 420 nm (preferably, 405 nm) and measuring the light emission (fluorescence) in a wavelength of 420 to 620 nm. More specifically, a solution containing a test sample and ThT is used as a measurement sample, a fluorescence lifetime measurement device (for example, compact fluorescence lifetime measurement device: Quantaurus-Tau, manufactured by Hamamatsu Photonics K.K.) is used, a fluorescence decay curve at excitation wavelength of 405 nm is measured from the wavelength of 420 nm to 620 nm at an interval of 10 nm based on time-correlated single photon counting method, the value of fluorescence decay curve is integrated over predetermined time (for example, 10 to 20 ns or so from the start of measurement), and the result is plotted against each wavelength. Accordingly, a time-resolved fluorescence spectrum can be obtained.

The time-resolved fluorescence spectrum is preferably a spectrum that is obtained by calibration of a background value. The background value can be a measurement value which is obtained by performing the same measurement for a measurement sample not containing ThT, for example. By subtracting the background value from a measurement value of a test sample, for example, the light emitting components that are not related with a test sample (for example, Raman scattered light) can be removed, and thus the Aβ oligomer can be detected with higher precision.

Normalization Step

In the normalization step, the time-resolved fluorescence spectrum of time period t1 to t2 and the time-resolved fluorescence spectrum of time period t3 to t4 are respectively normalized to obtain normalized spectra. In this regard, the relationship of $t1 < t2 \leq t3 < t4$ is satisfied.

The normalization means dividing the fluorescence intensity at each wavelength by the maximum fluorescence intensity of a time-resolved fluorescence spectrum. In a normalized spectrum after the normalization, the maximum value of relative fluorescence intensity is 1.

t1, t2, t3, and t4 may be either elapsed time when the time point at the start of fluorescence measurement is set at 0, or they may be elapsed time when the time point with 5% peak value increase of a fluorescence decay curve measured in the acquisition step is set at 0. In the latter case, t1, t2, t3, and t4 are generally at picosecond (ps) to microsecond (μs) order. Specifically, when the time point with 5% peak value increase of a fluorescence decay curve measured in the acquisition step is set at 0, it is generally $0 \text{ second} \leq t1 < t2 \leq t3 < t4 < 100$ nanoseconds (ns). It is preferably $0 \text{ second} \leq t1 < t2 \leq t3 < t4 < 50$ ns, and it is more preferably $0 \text{ second} \leq t1 < t2 \leq t3 < t4 < 30$ ns.

Determination Step

In the determination step, determination is made to confirm the presence or absence of an Aβ oligomer in a test sample on the basis of the two normalized spectra.

According to the detection method of this embodiment, shifting of the normalized spectrum of time period t3 to t4 towards the low wavelength side in comparison to the normalized spectrum of time period t1 to t2 indicates the presence of an Aβ oligomer in a test sample. As such, in the determination step, as long as the determination can be made regarding the shifting towards the low wavelength side, the determination can be made by using any means. Hereinbelow, specific examples of the determination means are described in detail. However, it is evident that the determination step is not limited to those specific examples.

According to the first determination means, the fluorescence ratio $s1$ is calculated from the value of fluorescence intensity at wavelength $\lambda 1$ of the two normalized spectra (with the proviso that, $\lambda 1 > 480$ nm) based on the following equation:

Fluorescence ratio $s1$=(Fluorescence intensity of normalized spectrum of time period $t3$ to $t4$ at wavelength $\lambda 1$)/(Fluorescence intensity of normalized spectrum of time period $t1$ to $t2$ at wavelength $\lambda 1$)

and when the fluorescence ratio s1 is less than 1, it is determined that an Aβ oligomer is present, or, when the fluorescence ratio s1 is 1 or more, it is determined that an Aβ oligomer is absent.

It is desirable that the wavelength λ1 is a wavelength that is longer than the peak top wavelength of the time-resolved fluorescence spectrum. In general, λ1 can be suitably set within a range of more than 480 nm and 600 nm or less. λ1 is 500 nm, for example. The peak top wavelength indicates a wavelength at which relative fluorescence intensity is 1.

According to the second determination means, the fluorescence ratio s2 is calculated from the value of fluorescence intensity at wavelength λ2 of the two normalized spectra (with the proviso that, λ2<480 nm) based on the following equation:

Fluorescence ratio s2=(Fluorescence intensity of normalized spectrum of time period t3 to t4 at wavelength λ2)/(Fluorescence intensity of normalized spectrum of time period t1 to t2 at wavelength λ2)

and when the fluorescence ratio s2 is more than 1, it is determined that an Aβ oligomer is present, or, when the fluorescence ratio s2 is 1 or less, it is determined that an Aβ oligomer is absent.

It is desirable that the wavelength λ2 is a wavelength that is shorter than the peak top wavelength of the time-resolved fluorescence spectrum. In general, λ2 can be suitably set within a range of 430 nm or more and less than 480 nm. λ2 is 460 nm, for example.

According to the third determination means, the peak top wavelength of the two normalized spectra is compared to each other and, when the peak top wavelength of the normalized spectrum of time period t3 to t4 is shorter than the peak top wavelength of the normalized spectrum of time period t1 to t2, it is determined that an Aβ oligomer is present, or, when the peak top wavelength of the normalized spectrum of time period t3 to t4 is the same or longer than the peak top wavelength of the normalized spectrum of time period t1 to t2, it is determined that an Aβ oligomer is absent.

Method for Collecting Data for Detecting Amyloid β Oligomer

The method for collecting data for detecting an Aβ oligomer according to this embodiment includes a step in which a test sample and thioflavin T are brought into contact with each other, a step in which fluorescence of the thioflavin T is measured to obtain time-resolved fluorescence spectra, and a step in which the time-resolved fluorescence spectrum of time period t1 to t2 and the time-resolved fluorescence spectrum of time period t3 to t4 are respectively normalized to obtain normalized spectra. The data obtained by this method (normalized spectrum of time period t1 to t2 and normalized spectrum of time period t3 to t4) can be used for determination of the presence or absence of an Aβ oligomer in a test sample.

Device for Detecting Amyloid β Oligomer

Figure 1:
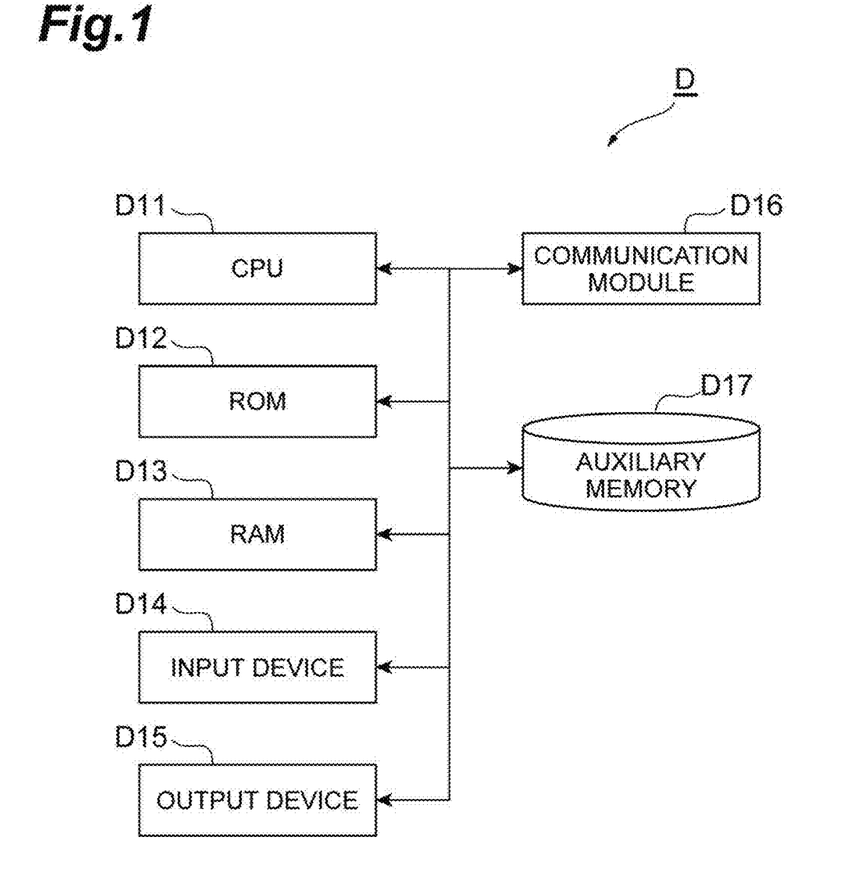
FIG. 1 is a schematic drawing illustrating the hardware constitution of Aβ oligomer detection device D.

Next, descriptions are given for the constitution of a device for detecting an Aβ oligomer. FIG. 1 is a schematic drawing illustrating the hardware constitution of amyloid β oligomer detection device D according to one embodiment, and FIG. 2 is a schematic drawing illustrating the functional constitution of Aβ oligomer detection device D according to one embodiment.

As shown in FIG. 1, a conventional computer which physically includes a CPU D11, a main memory such as ROM D12 and RAM D13, an input device D14 such as a keyboard and a mouse, an output device D15 such as a display, a communication module D16 such as a network card for transmission and reception of data in communication with other devices such as the imaging unit C, an auxiliary memory D17 such as a hard disk, and the like constitutes the Aβ oligomer detection device D. Each function of the Aβ oligomer detection device D described below can be realized by loading a given computer software on hardware such as CPU D11, ROM D12, and RAM D13, activating the input device D14, the output device D15, and the communication module D16 under control of the CPU D11, and reading and writing the data in the main memory D12 and D13 as well as the auxiliary memory D17.

Figure 2:
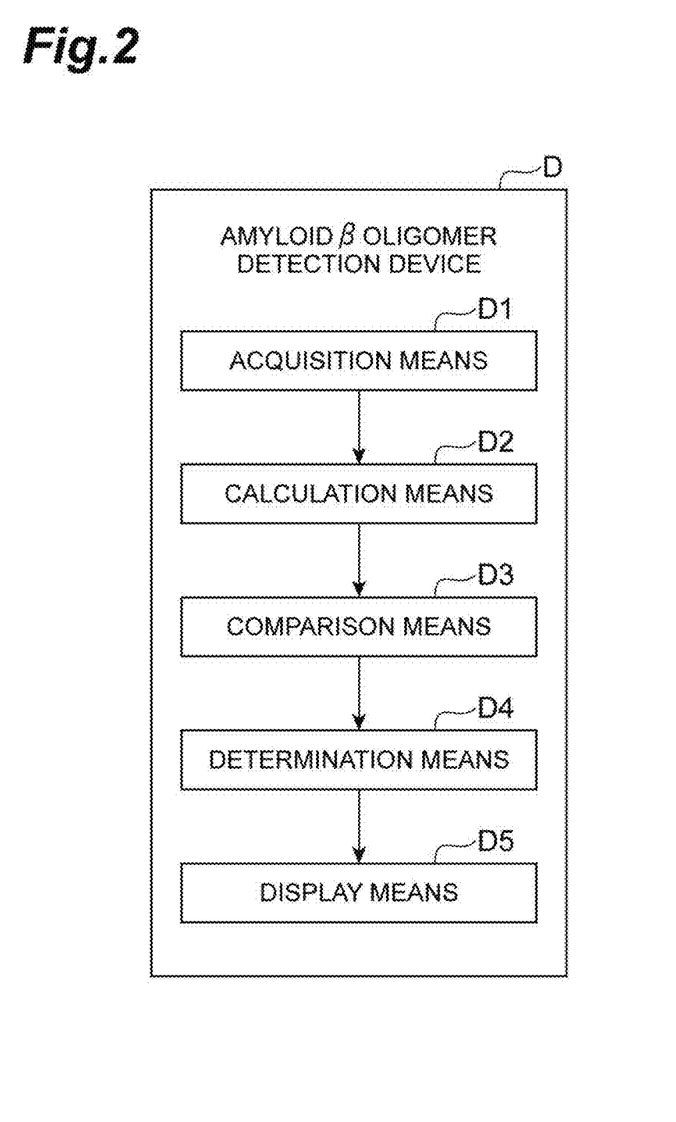
FIG. 2 is a schematic drawing illustrating the functional constitution of Aβ oligomer detection device D.

As shown in FIG. 2, the Aβ oligomer detection device D includes acquisition means D1, calculation means D2, comparison means D3, determination means D4, and display means D5, as functional components.

The acquisition means D1 acquires time-resolved fluorescence spectrum data obtained by using a fluorescence lifetime measurement device (not illustrated). The calculation means D2 calculates the aforementioned normalized spectrum from the acquired time-resolved fluorescence spectrum data. The comparison means D3 compares the normalized spectrum of time period t1 to t2 with the normalized spectrum of time period t3 to t4, which have been calculated. The determination means D4 determines detection of an Aβ oligomer based on the comparison data. The display means D5 is to display a determined result.

Program for Detecting Amyloid β Oligomer

The program for detecting an Aβ oligomer allows a computer to function as the acquisition means D1, the calculation means D2, the comparison means D3, the determination means D4, and the display means D5 that are described above. By loading the program for detecting an Aβ oligomer on the computer, the computer can function as the Aβ oligomer detection device D. The program for detecting an Aβ oligomer is provided, for example, by being stored in a computer-readable storage medium. The storage medium may be a non-transitory storage medium. The storage medium is exemplified by a storage medium such as a flexible disc, CD, or DVD, a storage medium such as ROM, and a semiconductor memory, or the like.

Method for Detecting Amyloid β Oligomer

Figure 3:
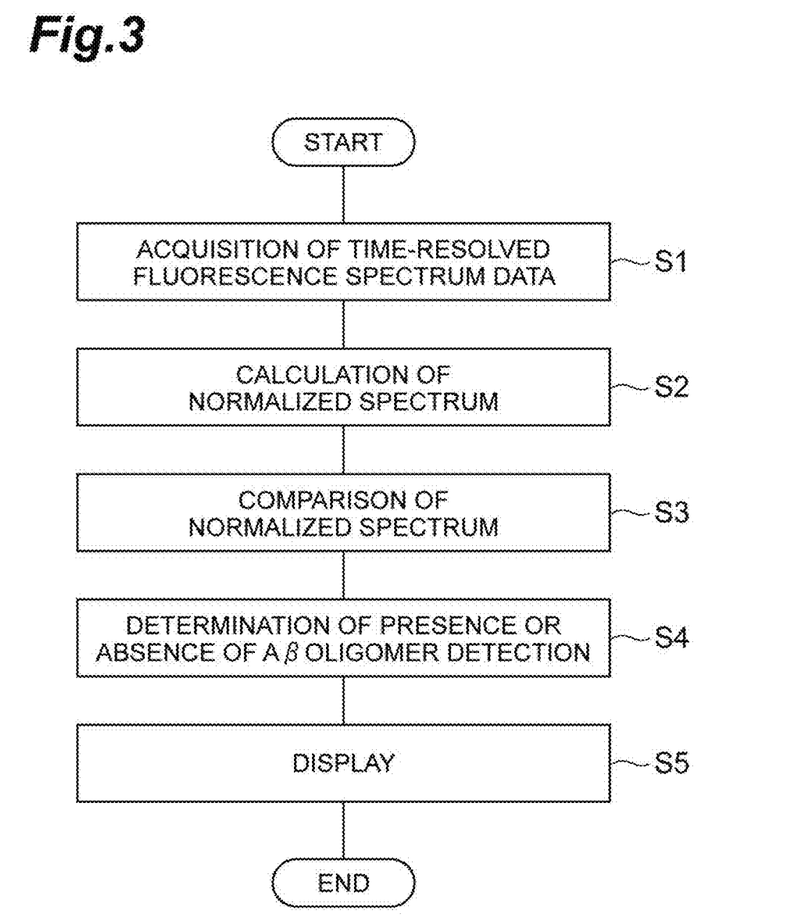
FIG. 3 is a flow chart illustrating a method for detecting an Aβ oligomer.

Descriptions are given for a method for detecting an Aβ oligomer by using Aβ oligomer detection device D. FIG. 3 is a flow chart illustrating a method for detecting an Aβ oligomer. According to the method for detecting an Aβ oligomer which is performed by using oligomer detection device D, determination of the presence or absence of an Aβ oligomer in a test sample can be carried out automatically with high precision.

Acquisition Step S1

First of all, time-resolved fluorescence spectrum data are acquired by acquisition means D1 from a fluorescence measurement device.

Calculation Step S2

Next, a normalized spectrum is calculated from the time-resolved fluorescence spectrum data which has been acquired by calculation means D2.

Comparison Step S3

Next, by comparison means D3, the normalized spectrum of time period t1 to t2 is compared with the normalized spectrum of time period t3 to t4, which have been calculated in calculation step S2, and the results are extracted.

Determination Step S4

Next, based on the comparison results which have been extracted in comparison step S3, detection of an Aβ oligomer (presence or absence of Aβ oligomer in test sample) is determined by determination means D4.

Display Step S5

Next, the determination results of determination step S4 are displayed by display means D5. For example, the presence or absence of an Aβ oligomer in a test sample is displayed by display means D5.

EXAMPLES

Hereinbelow, the present invention is descried more specifically on the basis of Examples. However, it is evident that the present invention is not limited to the following Examples.

Example 1: Identification of Aβ Oligomer and Aβ Fibril (1)

Preparation of Aβ Oligomer

Based on the method described in the Non Patent Literature (J. Biol. Chem., 2003, Vol. 278 (No. 13), pp. 11612-11622), an Aβ oligomer was prepared according to the following order. First, Aβ1-42 (trade name: Amyloid β-protein Human, 1-42, manufactured by PEPTIDE INSTITUTE, INC.) was dissolved in dimethyl sulfoxide to have 5 mmol/L, and, by using Ham's medium (containing L-glutamine, but no phenol red), it was diluted to have Aβ1-42 concentration of 100 μmol/L. The obtained Aβ solution was incubated for 24 hours at 4° C. by using an incubator. By performing the incubation, a sample containing an Aβ oligomer (Aβ oligomer) was prepared.

Preparation of Aβ Fibril

Based on the method described in the aforementioned non patent literature, Aβ fibril was prepared according to the following order. First, Aβ1-42 was dissolved in dimethyl sulfoxide to have 5 mmol/L, and, by using Ham's medium (containing L-glutamine, but no phenol red), it was diluted to have Aβ1-42 concentration of 100 μmol/L. The obtained Aβ solution was incubated for 24 hours at 37° C. by using an incubator. By performing the incubation, a sample containing an Aβ fibril (Aβ42 fibril) was prepared.

ThT Staining 3.4 mg of ThT (manufactured by AAT Bioquest Inc.) was dissolved in 20 mL of pure water to prepare a ThT solution. Because fluorescent impurities are included in this aqueous solution, the aqueous solution was added to a separating funnel, added with 50 mL of hexane, and mixed thoroughly to perform an extraction operation. After that, from a cock at the lower side of the separating funnel, the ThT solution was extracted. Part of the ThT solution was collected in a cuvette and used for measurement of fluorescence intensity with excitation wavelength of 350 nm and observation wavelength of 440 nm by using fluorescence spectrophotometer RF-5000 (manufactured by SHIMADZU CORPORATION). The extraction operation was repeated 10 times until the fluorescence intensity reaches the level of background (until the measurement value of fluorescence intensity does not decrease anymore). The ThT solution used for staining was prepared by diluting the ThT solution not containing fluorescent impurities, which has been prepared by the above operation, with distilled water till to have ThT concentration of 100 μmol/L. To 10 μL of a sample which includes an Aβ oligomer or Aβ fibril, 20 μL of 100 μmol/L aqueous ThT solution and 220 μL of 50 mmol/L glycine-sodium hydroxide solution (pH 9.0) were added and mixed with each other to have ThT staining.

Measurement of Fluorescence

The stained sample was aliquoted to a quartz cell having inner diameter of 3 mm, and by using a compact fluorescence lifetime measurement device (Quantaurus-Tau, manufactured by Hamamatsu Photonics K.K.) and a time-correlated single photon counting method, the fluorescence decay curve at excitation wavelength of 405 nm was measured from 420 nm to 620 nm at an interval of 10 nm. The 5% increase point in peak value of the measured fluorescence decay curve was set as time 0, and each of the measurement value of the fluorescence decay curve for time period 0 to 2 ns and time period 10 to 18 ns was integrated. Then, by plotting the value which is obtained by subtracting the background value from the integrated value against wavelength, a time-resolved fluorescence spectrum was obtained. The background value indicates a value which is obtained by measuring, according to the same method as above, a sample in which 240 μL of distilled water is added and mixed with 10 μL of Ham's medium (containing L-glutamine, but no phenol red).

Normalized Spectrum

For each time-resolved fluorescence spectrum, the fluorescence intensity at each wavelength was divided by the maximum value of fluorescence intensity, and normalization was carried out such that the maximum value of fluorescence intensity corresponds to 1.

Determination

Figure 4:
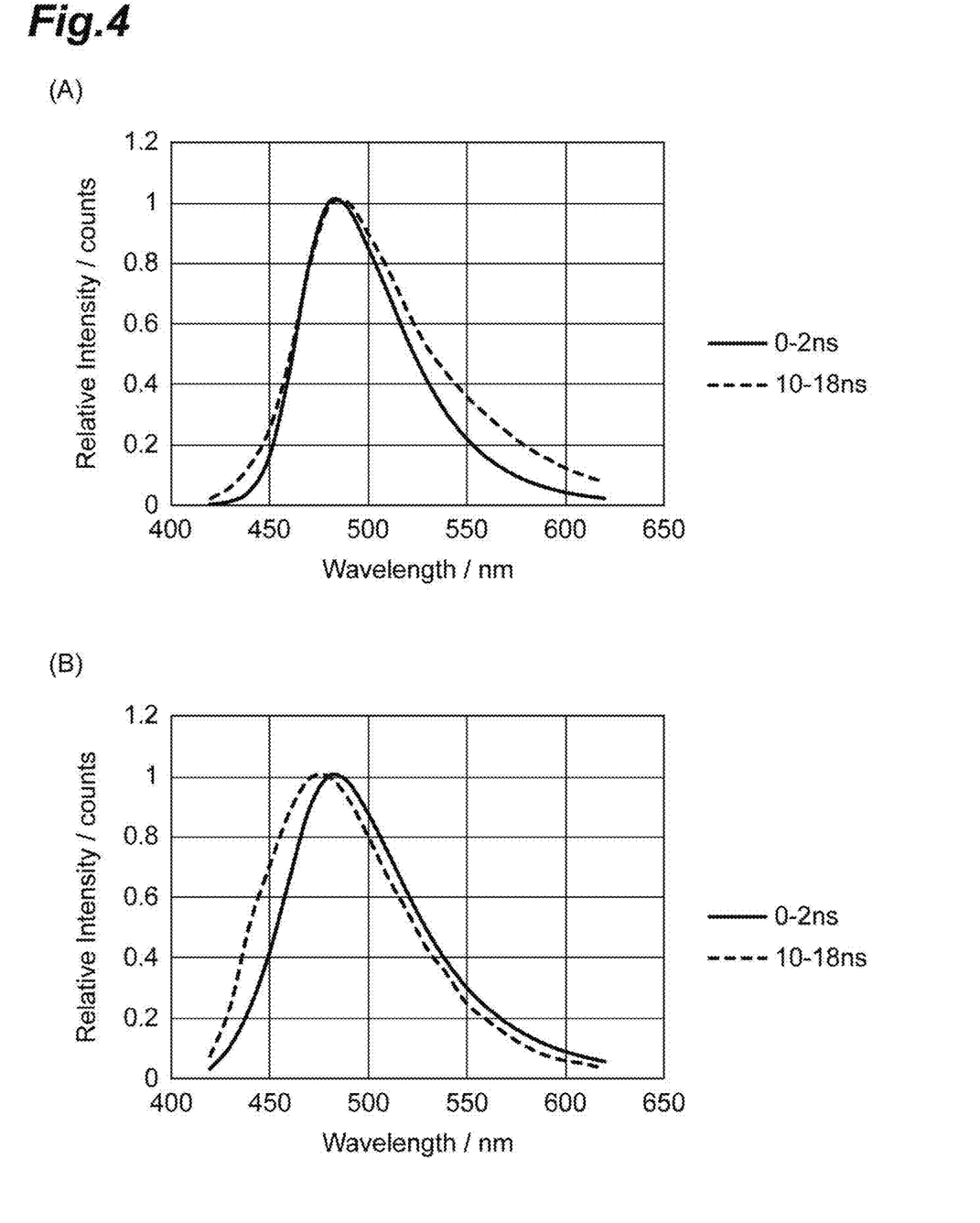

The normalized spectra for the time period 0 to 2 ns and time period 10 to 18 ns, which have been obtained as described above, were shown respectively in FIG. 4. FIG. 4(A) is a normalized spectrum of Aβ42 fibril, and FIG. 4(B) is a normalized spectrum of Aβ42 oligomer. When comparison is made between the normalized spectrum for the time period 0 to 2 ns and the normalized spectrum for the time period 10 to 18 ns, it was found that, while a slight shifting towards the long wavelength is shown with Aβ fibril, a clear shifting towards the short wavelength is shown with an Aβ oligomer.

Based on the above shifting towards the short wavelength, identification of an Aβ oligomer was made by using the following equation for determination. A wavelength longer than the peak top wavelength of the normalized spectrum for the time period 0 to 2 ns was selected (in Example 1, 500 nm), and the ratio (fluorescence ratio s) between the fluorescence intensity of normalized spectrum for the time period 10 to 18 ns and the fluorescence intensity of normalized spectrum for the time period 0 to 2 ns at the selected wavelength was calculated based on the following.

Fluorescence ratio s=Fluorescence intensity of normalized spectrum of time period 10 to 18 ns (wavelength of 500 nm)/Fluorescence intensity of normalized spectrum of time period 0 to 2 ns (wavelength of 500 nm)

Figure 5:
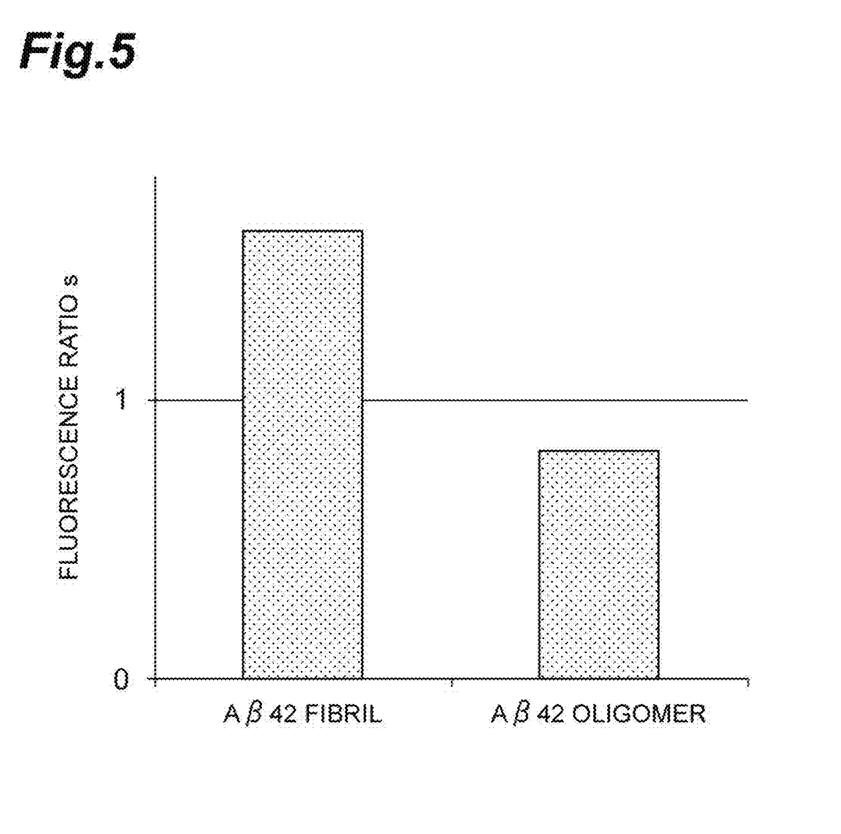
FIG. 5 is a graph illustrating the fluorescence ratio s which has been calculated from normalized spectra of Aβ42 fibril and Aβ42 oligomer.

The fluorescence ratio s which has been calculated as above is shown in FIG. 5. As shown in FIG. 5, the fluorescence ratio s of Aβ fibril (Aβ42 fibril) was 1 or more, but the fluorescence ratio s of Aβ oligomer (Aβ42 oligomer) was less than 1. Namely, an Aβ oligomer can be identified by the fluorescence ratio s of less than 1. Furthermore, as a result of repeating the experiments with various conditions, the inventors of the present invention confirmed that the aforementioned determination method is suitable in general.

Example 2: Identification of Aβ Oligomer and Aβ Fibril (2)

Example 2 was carried out according to the same order as Example 1 except that the preparation and fluorescence measurement of Aβ fibril are carried out by following the method described below.

Preparation of Aβ Fibril

First, Aβ1-40 (trade name: Amyloid β-protein Human, 1-40, manufactured by PEPTIDE INSTITUTE, INC.) was dissolved in dimethyl sulfoxide to have 5 mmol/L, and, by using 50 mM sodium phosphate buffer solution (pH 7.4), it was diluted to have Aβ1-40 concentration of 100 μmol/L. The obtained Aβ solution was incubated for 10 days at 37° C. by using an incubator. By performing the incubation, a sample containing Aβ fibril (Aβ40 fibril) was prepared.

Measurement of Fluorescence

The stained sample was aliquoted to a quartz cell having inner diameter of 3 mm, and by using a compact fluorescence lifetime measurement device (Quantaurus-Tau, manufactured by Hamamatsu Photonics K.K.) and a time-correlated single photon counting method, the fluorescence decay curve at excitation wavelength of 405 nm was measured from 420 nm to 620 nm at an interval of 10 nm. The 5% increase point in peak value of the measured fluorescence decay curve was set as time 0, and each of the measurement value of the fluorescence decay curve for time period 0 to 2 ns and time period 10 to 18 ns was integrated. Then, by plotting the value which is obtained by subtracting the background value from the integrated value against wavelength, a time-resolved fluorescence spectrum was obtained. The background value indicates a value which is obtained by measuring, according to the same method as above, a sample in which 240 μL of distilled water is added and mixed with 10 μL of 50 mM sodium phosphate buffer solution (pH 7.4).

Determination

Figure 6:
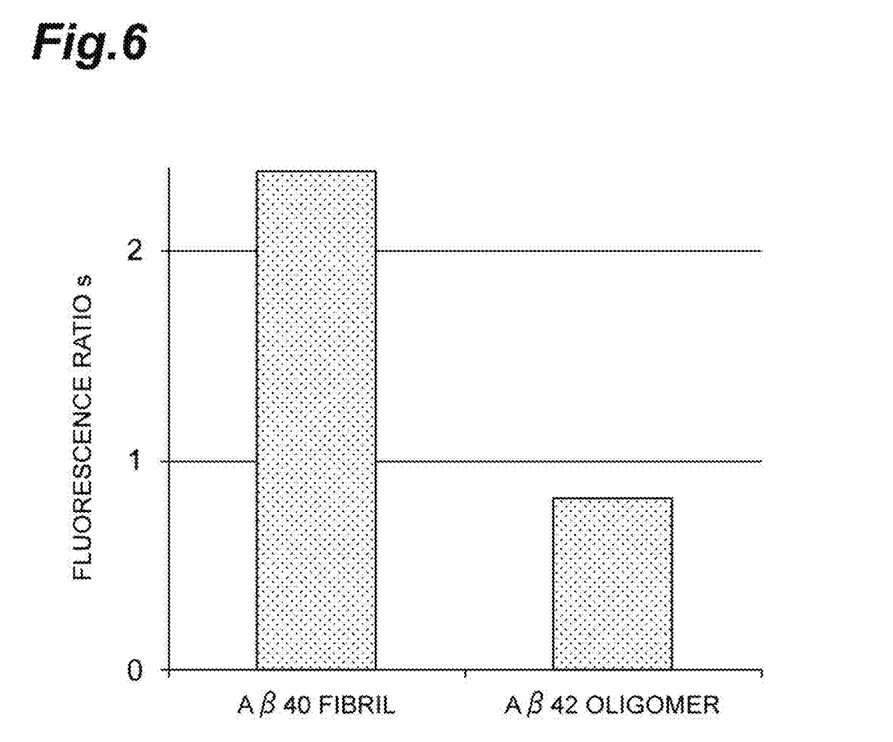
FIG. 6 is a graph illustrating the fluorescence ratio s which has been calculated from normalized spectra of Aβ40 fibril and Aβ42 oligomer.

The fluorescence ratio s was calculated in the same manner as Example 1. The calculated fluorescence ratio s is shown in FIG. 6. As it is shown in FIG. 6, the fluorescence ratio s of Aβ fibril (Aβ40 fibril) is 1 or more even when the type of Aβ monomer is different. Namely, it was shown that, even when there is Aβ fibril consisting of Aβ monomer of different type, Aβ oligomer (Aβ42 oligomer) can be identified according to the same order as Example 1.

Example 3: Identification of Aβ Oligomer and Aβ Fibril (3)

Example 3 was carried out according to the same order as Example 1 except that the preparation of Aβ oligomer and preparation and fluorescence measurement of Aβ fibril are carried out by following the method described below.

Preparation of Aβ Oligomer

First, Aβ1-40 (trade name: Amyloid β-protein Human, 1-40, manufactured by PEPTIDE INSTITUTE, INC.) was dissolved in dimethyl sulfoxide to have 5 mmol/L, and, by using 50 mM sodium phosphate buffer solution (pH 7.4), it was diluted to have Aβ1-40 concentration of 100 μmol/L. The obtained Aβ solution was incubated for 1 day at 37° C. by using an incubator. By performing the incubation, a sample containing Aβ oligomer (Aβ40 oligomer) was prepared.

Preparation of Aβ Fibril

First, Aβ1-40 (trade name: Amyloid β-protein Human, 1-40, manufactured by PEPTIDE INSTITUTE, INC.) was dissolved in dimethyl sulfoxide to have 5 mmol/L, and, by using 50 mM sodium phosphate buffer solution (pH 7.4), it was diluted to have Aβ1-40 concentration of 100 μmol/L. The obtained Aβ solution was incubated for 7 days at 37° C. by using an incubator. By performing the incubation, a sample containing Aβ fibril (Aβ40 fibril) was prepared.

Measurement of Fluorescence

The stained sample was aliquoted to a quartz cell having inner diameter of 3 mm, and by using a compact fluorescence lifetime measurement device (Quantaurus-Tau, manufactured by Hamamatsu Photonics K.K.) and a time-correlated single photon counting method, the fluorescence decay curve at excitation wavelength of 405 nm was measured from 420 nm to 620 nm at an interval of 5 nm. The 5% increase point in peak value of the measured fluorescence decay curve was set as time 0, and each of the measurement value of the fluorescence decay curve for time period 0 to 2 ns and time period 10 to 18 ns was integrated. Then, by plotting the value which is obtained by subtracting the background value from the integrated value against wavelength, a time-resolved fluorescence spectrum was obtained. The background value indicates a value which is obtained by measuring, according to the same method as above, a sample in which 240 μL of 50 mmol/L glycine-sodium hydroxide solution (pH 9.0) were added and mixed with 10 μL of 50 mM sodium phosphate buffer solution containing 0.8% DMSO (pH 7.4).

Determination

Figure 7:
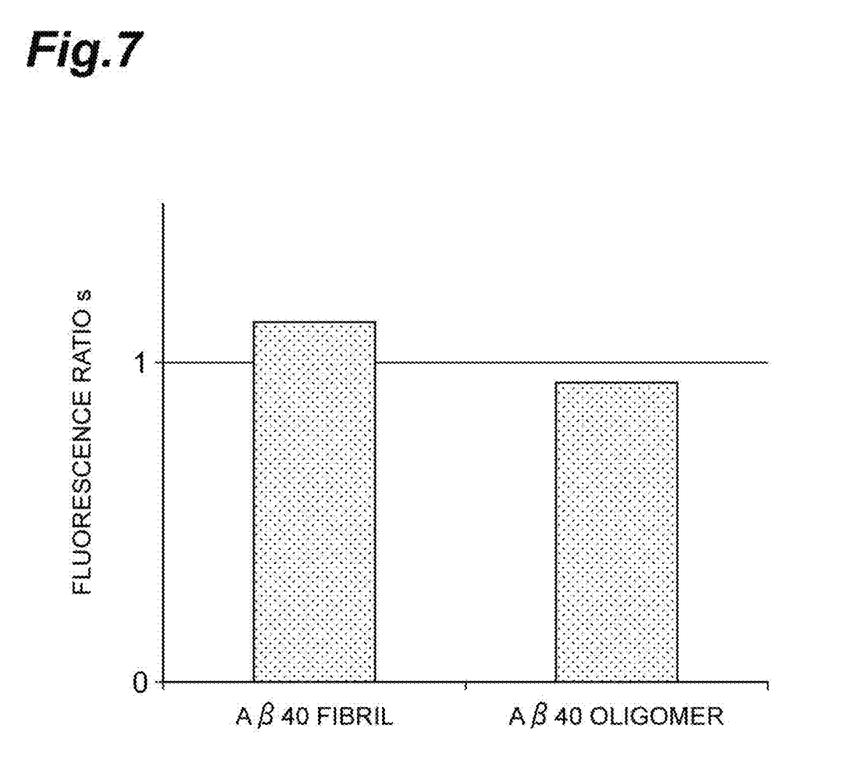
FIG. 7 is a graph illustrating the fluorescence ratio s which has been calculated from normalized spectra of Aβ40 fibril and Aβ40 oligomer.

The fluorescence ratio s was calculated in the same manner as Example 1. The calculated fluorescence ratio s is shown in FIG. 7. As it is shown in FIG. 7, the fluorescence ratio s of Aβ oligomer (Aβ40 oligomer) is less than 1 while the fluorescence ratio s of Aβ fibril (Aβ40 fibril) is 1 or more. Namely, it was shown that an Aβ oligomer (Aβ40 oligomer) can be identified according to the same order as Example 1.

REFERENCE SIGNS LIST

D . . . Device for detecting amyloid β oligomer, D1 . . . Acquisition means, D2 . . . Calculation means, D3 . . . Comparison means, D4 . . . Determination means, D5 . . . Display means, D11 . . . CPU, D12 . . . ROM, D13 . . . RAM, D14 . . . Input device, D15 . . . Output device, D16 . . . Communication module, D17 . . . Auxiliary memory device.

The invention claimed is:

1. A method for detecting an amyloid β oligomer, comprising:
a step in which a test sample and thioflavin T are brought into contact with each other;
a step in which fluorescence of the thioflavin T is measured to obtain time-resolved fluorescence spectra;
a step in which the time-resolved fluorescence spectrum of time period t1 to t2 and the time-resolved fluorescence spectrum of time period t3 to t4 are respectively normalized to obtain normalized spectra; and
a step in which determination is made to confirm the presence or absence of an amyloid β oligomer in the test sample on the basis of the two normalized spectra, wherein t1<t2≤t3<t4, and
shifting of the normalized spectrum of time period t3 to t4 towards a low wavelength side in comparison to the normalized spectrum of time period t1 to t2 indicates the presence of an amyloid β oligomer in the test sample.

2. The method for detecting an amyloid β oligomer according to claim 1,
wherein, in the step for determination, fluorescence ratio s1 is calculated from the value of fluorescence intensity at wavelength λ1 of the two normalized spectra based on the following equation:

Fluorescence ratio $s1$=(Fluorescence intensity of normalized spectrum of time period $t3$ to $t4$ at wavelength λ1)/(Fluorescence intensity of normalized spectrum of time period $t1$ to $t2$ at wavelength λ1), and when the fluorescence ratio s1 is less than 1, it is determined that an amyloid β oligomer is present, or, when the fluorescence ratio s1 is 1 or more, it is determined that an amyloid β oligomer is absent,
wherein λ1 is more than 480 nm.

3. The method for detecting an amyloid β oligomer according to claim 1,
wherein, in the step for determination, fluorescence ratio s2 is calculated from the value of fluorescence intensity at wavelength λ2 of the two normalized spectra based on the following equation:

Fluorescence ratio $s2$=(Fluorescence intensity of normalized spectrum of time period $t3$ to $t4$ at wavelength λ2)/(Fluorescence intensity of normalized spectrum of time period $t1$ to $t2$ at wavelength λ2), and when the fluorescence ratio s2 is more than 1, it is determined that an amyloid β oligomer is present, or, when the fluorescence ratio s2 is 1 or less, it is determined that an amyloid β oligomer is absent,
wherein λ2 is less than 480 nm.

4. The method for detecting an amyloid β oligomer according to claim 1,
wherein, in the step for determination, comparison of a peak top wavelength of the two normalized spectra is made, and
when the peak top wavelength of the normalized spectrum of time period t3 to t4 is shorter than the peak top wavelength of the normalized spectrum of time period t1 to t2, it is determined that an amyloid β oligomer is present, or, when the peak top wavelength of the normalized spectrum of time period t3 to t4 is the same or longer than the peak top wavelength of the normalized spectrum of time period t1 to t2, it is determined that an amyloid β oligomer is absent.

* * * * *